United States Patent [19]

Nagy et al.

[11] 4,283,955

[45] Aug. 18, 1981

[54] METHOD OF AND MEASURING APPARATUS FOR DETERMINING THE STANDARD TENSILE YIELD POINT UNDER LOAD CONDITIONS

[75] Inventors: Ferenc Nagy; Ferenc Szabó; Zoltan Szücs, all of Szekesfehervar, Hungary

[73] Assignee: Magyar Aluminiumipari Troszt, Budapest, Hungary

[21] Appl. No.: 53,751

[22] Filed: Jul. 2, 1979

[30] Foreign Application Priority Data

Jul. 4, 1978 [HU] Hungary .............................. AU 405

[51] Int. Cl.³ .............................................. G01N 3/08
[52] U.S. Cl. ....................................... 73/772; 73/789; 73/826; 364/508
[58] Field of Search ................. 73/761, 772, 789, 826; 364/508

[56] References Cited

U.S. PATENT DOCUMENTS

| | | | |
|---|---|---|---|
| 3,076,603 | 2/1963 | Gruber | 73/772 X |
| 3,554,019 | 1/1971 | Hove et al. | 73/772 |
| 3,558,866 | 1/1971 | Poulson | 364/508 |
| 3,733,049 | 5/1973 | Hove et al. | 73/826 X |

Primary Examiner—James J. Gill
Attorney, Agent, or Firm—Manfred M. Warren; Robert B. Chickering; Glen R. Grunewald

[57] ABSTRACT

A method of and apparatus for the determination of the standard tensile yield point in which the extension of a test body is monitored, comprises determining in the course of continuous extension within the elastic limit, the ratio of the instantaneous extension and the associated load, storing this ratio and in the course of further continuous extension the ratios of a given residual extension as well as that of the instantaneous extension and the instantaneous load are determined, the stored ratio value is summed with the ratio of the given residual extension and the instantaneous load, and the thus obtained sum is compared with the ratio of the instantaneous load whereby the instantaneous load at which the compared values become substantially equal gives the tensile yield stress at the given residual.

3 Claims, 2 Drawing Figures

METHOD OF AND MEASURING APPARATUS FOR DETERMINING THE STANDARD TENSILE YIELD POINT UNDER LOAD CONDITIONS

This invention concerns a method of and measuring apparatus for determining the standard tensile yield point under load conditions.

According to Hungarian standard MSz 105-72, the standard or conventional tensile yield point must be determined from the rupture diagram by drawing from a point A on the abscissa which represents an extension of predetermined magnitude (generally 0.2%) a line parallel with the initial straight section of the curve. The straight line intersects the curve at the standard tensile yield point or at that value of the load which, after dividing it with the original cross-sectional area, gives the standard yield point, see FIG. 1.

In this standard measurement, the force or load P is continuously registered or recorded as a function of the extension of the test body. The registration or recording is principally effected by means of a co-ordinate writer. The value $R_p$ i.e. the sought tensile yield point can be determined from the thus obtained diagram by a subsequent evaluation process. A disadvantage of this solution is that it is not suitable for industrial scale measurements because the total time required which includes evaluation time makes it highly time-consuming and requires highly skilled personnel; furthermore, the risk of committing subjective errors is high. The use of a co-ordinate writer makes the measurement cumbersome and expensive.

An aim of the invention is to provide a process in which the determination of the standard tensile yield point for a standard tensile rupture body can be achieved without any increase in the time required for the test and without disturbing the determination of other mechanical parameters. A further aim is to provide measurement apparatus for carrying out the process with which the above-mentioned disadvantages can be eliminated and which from the point of view of cost should also be affordable by industrial laboratories. Its handling should be simple so as not to require special training and skill.

In the course of the process according to the invention, the extension of the test body is monitored so that in the course of continuous extension the ratio or quotient of the instantaneous extension within the elastic limit and the applied load associated with this instantaneous extension is determined and stored, whereafter in the course of further continuous extension the residual extension as well as the quotients or ratios of the instantaneous extension and the instantaneous load are determined. The sum of the ratio within the elastic limit and the ratio of the residual extension is obtained and this sum is compared with the ratio taken beyond the elastic limit. When the sum and the ratio are equal or in agreement the instantaneous load gives the standard tensile yield point.

The process according to the invention can be carried out by means of a measuring instrument, which can be placed on the test body and contains an extensometer providing an electrical signal proportional to the longitudinal extension of the test body and a dynamometer or other force-measuring instrument providing an electrical output signal proportional to the applied load. The output of the extensometer is connected to a first transducer while the output of the dynamometer is connected to a second transducer. The transducers are connected to a first dividing unit while the output of the first transducer is connected also with one input of a first store, the second input of which is connected to the output of the first dividing unit. The second transducer is also connected to one input of a second dividing unit, the second input of which is connected to a reference unit. The output of the second dividing unit and the output of the first store are connected to the inputs of a summing unit the output of which is connected to one input of a comparator, the other input of which is connected to the output of the first dividing unit. The output of the comparator is connected to one input of a second store and the second transducer is connected to the second input of the second store. An indicator device or recording device is connected to the output of the second store.

The advantage of the solution according to the invention is that the time required for measurement is small, the operation of the apparatus is reliable, errors are negligible and its handling or operation is simple and inexpensive. A preferred embodiment of the invention is described with reference to the accompanying drawings in which.

In the process according to the invention, the standard tensile yield point $R_p$ under load is determined without a co-ordinate writer, without subsequent evaluation and without the use of computing machines in the course of the standard rupture tests by subjecting the test body to continuous strain or extension in the course of which the ratio or quotient of the arbitrary instantaneous extension within the elastic limit (resilient change of shape) and the load associated with the instantaneous extension is determined. The thus obtained value of the ratio or quotient is stored. Then in the course of further extension the ratio of a given residual extension and the associated given instantaneous load is formed as well as the ratio of the instantaneous extension and the instantaneous load and these are summed. The thus obtained sum is compared with the stored value. In the event of equality, i.e. when the ratio of the extension to load within the elastic limit plus the ratio of the residual extension to the instantaneous load equals the ratio of the instantaneous extension to instantaneous load, then this instantaneous load gives the value of the standard tensile yield point $R_p$.

This may be expressed mathematically as follows:

$$\lambda_R/P + \lambda_L/P_L = \lambda/P$$

where $\lambda$ and $P$ are the instantaneous extension and load respectively, $\lambda_R$ is the residual extension and $\lambda_L$ and $P_L$ are the extension and load within the elastic limit.

This equation may be rewritten in the following form:

$$(\lambda - \lambda_R)/P = \lambda_L/P_L$$

Figure 1:
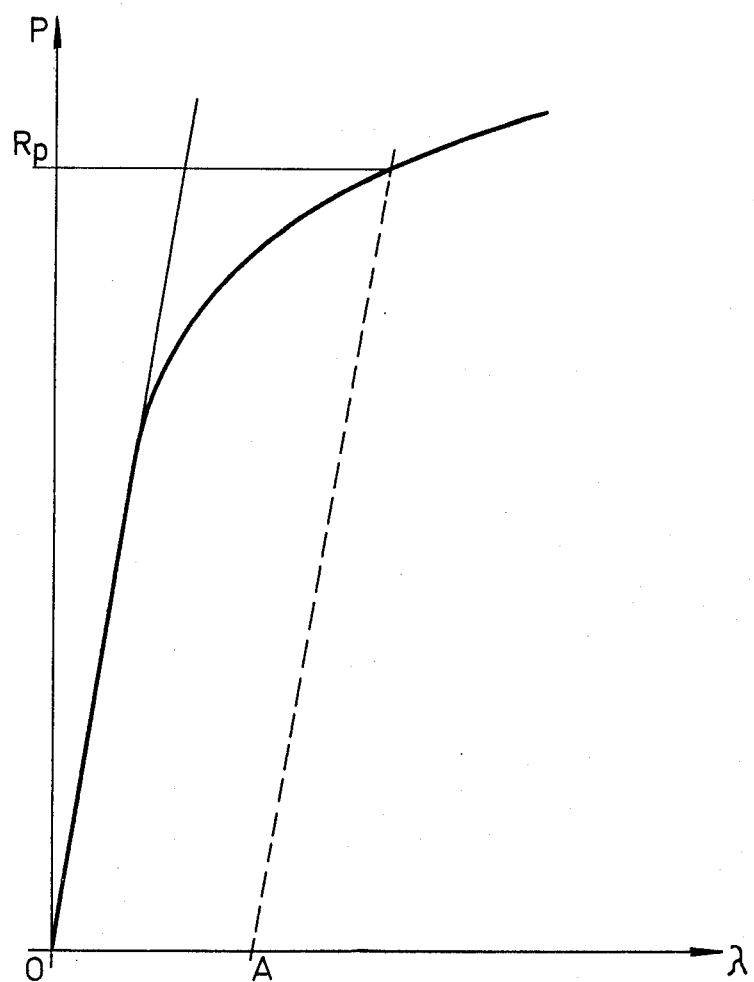
FIG. 1 illustrates the graphical method representing the state of the art.
Figure 2:
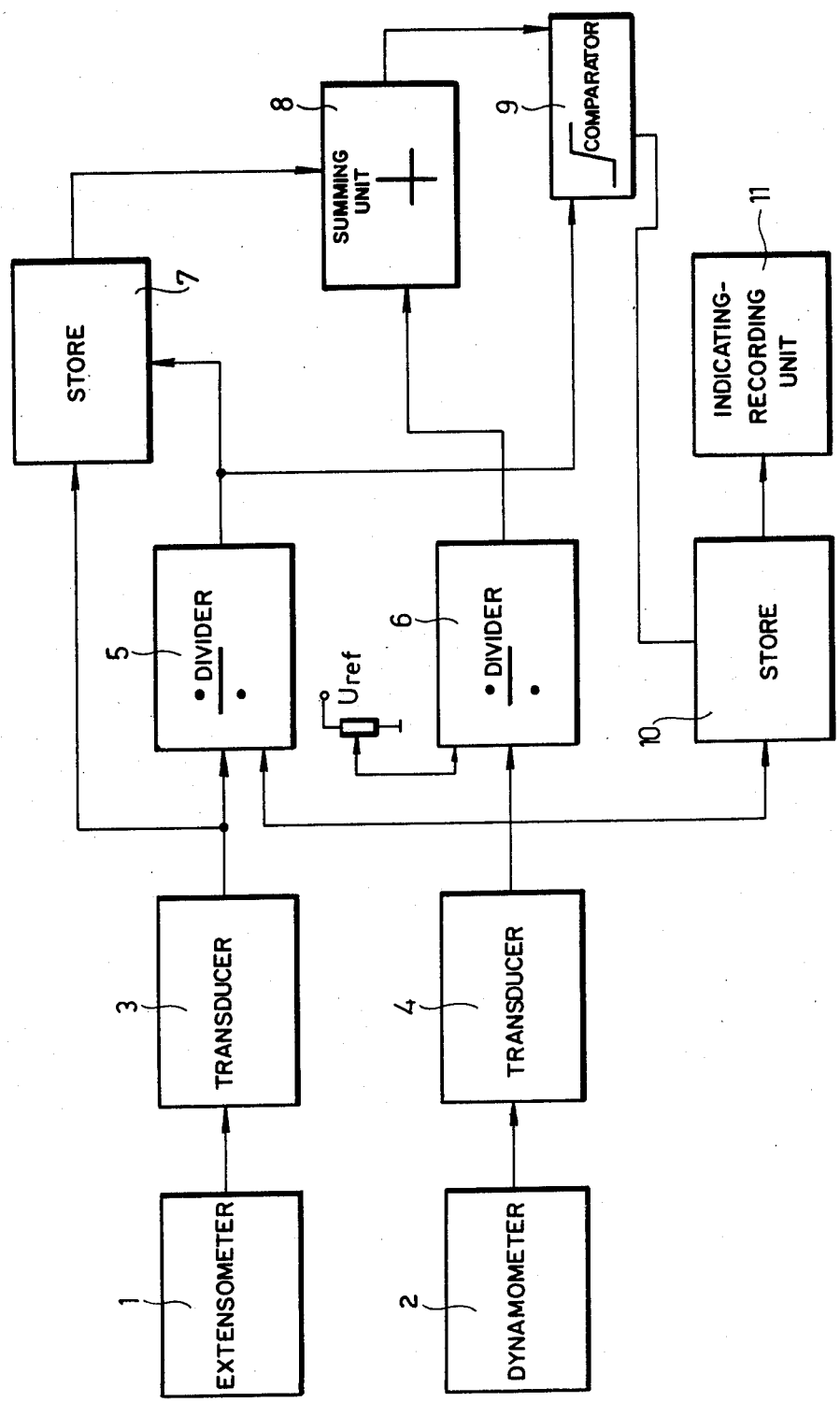
FIG. 2 is a connection diagram of a measurement instrument according to the present invention.

The left hand term represents the slope of a line drawn between the point A on the abscissa and a point on the curve represented by the instantaneous extension and load values $\lambda$ and $P$, while the right hand side of the equation represents the slope at the linear part of the curve within the elastic limit. It will be apparent therefore that when the two lines are parallel, the tensile yield point has been reached. The measurement apparatus thus in effect continuously monitors the slope of the dotted line in FIG. 1 and when, as shown in FIG. 1, it is of equal slope to the linear part of the curve (solid line) produces an indication of the load value $R_p$ at that instant.

The measurement apparatus consists of an extensometer 1 that can be placed on the test body and which provides an electric signal proportional to the longitudinal extension of the test body. The apparatus is further provided by a dynamometer 2 which provides an electric signal proportional to the load exerted on the test body. The output of the extensometer 1 is connected to a first transducer 3 while the output of the dynamometer 2 is connected to a second transducer 4. The transducers 3 and 4 are such as to enable different types of extensometers and dynamometers to be used. The outputs of the transducers 3 and 4 are connected to a first dividing unit 5 to form the quotient of the instantaneous extension and the associated load of the test body. The respective outputs of the first transducer 3 and of the first dividing unit 5 are connected to inputs of a first store 7. The first store 7 is arranged to store the instantaneous quotient or ratio from the first divider unit 5 applied to one of its inputs, when the output from the first transducer 3 applied to its other input reaches a predetermined extension value within the elastic limit so that the stored ratio is characteristic of the linear section of the stress strain diagram i.e. the section within the elastic limit (resilient change of shape). The second transducer 4 is connected to one input of a second dividing unit 6 which receives from a reference unit $U_{ref}$ connected to its other input a preset reference voltage corresponding to the residual extension value (quantity OA of FIG. 1) for which the tensile yield point is required, to give an output value representing the ratio of the residual extension to the instantaneous load. The outputs of the second dividing unit 6 and of the first store 7 are connected to respective inputs of a summing unit 8. The summing unit 8 continuously forms the sum of the signals from the second dividing unit 6 and the first store 7. The output of the summing unit 8 is connected to one input of a comparator unit 9 while the other input of the comparator unit 9 is connected to the output of the first dividing unit 5. The comparator 9 compares the electric signals received from the summing unit 8 with the electric signal coming from the dividing unit 5. If the compared signals are equal, then a control signal is passed by the comparator to a second store 10. The second input of the second store 10 is connected with the second transducer 4 and under the effect of a control signal, stores the instantaneous force value appearing on its second input which gives the tensile yield point $R_p$ it is desired to measure. The indicating/recording unit 11 connected with the output of the second store 10 indicates the stored force or load or some conventional voltage value corresponding thereto, in an analog or digital manner.

The apparatus according to the invention utilises the electric signals which are proportional to the longitudinal extension of the test body and to the load automatically indicates in analog or digital form a preset arbitrary load or a proportional voltage associated with the residual change or shape without further intervention or further evaluation.

Handling of the apparatus requires no special technical skill since the extensometer pick-up can be simply placed on the test body while the desired residual extension can be preset with the aid of the manipulating or handling means of the apparatus. Then thereafter without further interference, the apparatus is set in operation and other conventional mechanical parameters, such as $R_m:\delta_{10}$ can be determined without the need for intervention to give the desired $R_p$ value.

Compared with known measurement methods, the time requirement of the present invention is smaller and has considerable advantages also for reducing both costs and measurement errors.

What is claimed is:

1. A method of determining the standard tensile yield point in which the extension of a test body is monitored, wherein in the course of continuous extension within the elastic limit, the ratio of the instantaneous extension and the associated load is determined and stored, and in the course of further continuous extension the ratios of a given residual extension as well as that of the instantaneous extension and the instantaneous load are determined, the stored ratio value is summed with the ratio of the given residual extension and the instantaneous load, and the thus obtained sum is compared with the ratio of the instantaneous extension and the instantaneous load whereby the instantaneous load at which the compared values become substantially equal gives the tensile yield stress at the given residual extension.

2. Apparatus for carrying out the method in claim 1, comprising means for determining in the course of continuous extension, within the elastic limit, the ratio of the instantaneous extension and the associated load, means for storing this ratio, means for determining, in the course of further continuous extension, the ratios of a given residual extension as well as that of the instantaneous extension and the instantaneous load, means for summing the stored ratio value with the ratio of the given residual extension and the instantaneous load, and means for comparing the thus obtained sum with the ratio of the instantaneous extension and the instantaneous load.

3. Apparatus according to claim 2, and including an extensometer adapted to be placed on a test body and to give electrical signals proportional to the longitudinal extension of the test body, a dynamometer for giving an electrical signal proportional to the applied load, the outputs of the extensometer and the dynamometer being connected with a first and a second transducer, respectively the transducer output being connected to first dividing unit, while the output of the first transducer is also connected to one input of a first store the second input of which is connected to the output of the first dividing unit; the output of the second transducer is connected to one input of a second dividing unit the other input of which is connected to a reference unit while the outputs of the second dividing unit and the first store are each connected to inputs of a summing unit the output of which is connected to one input of a comparator the other input of which is connected to the output of the first dividing unit, and the output of the comparator is connected to one input of the second store, while the output of the second transducer is also connected to the other input of the second store, and an indicating/recording unit is connected to the second store.

* * * * *

UNITED STATES PATENT AND TRADEMARK OFFICE
CERTIFICATE OF CORRECTION

PATENT NO. : 4,283,955

DATED : August 18, 1981

INVENTOR(S) : Ferenc Nagy; Ferenc Szabo; Zoltan Szucs

It is certified that error appears in the above—identified patent and that said Letters Patent are hereby corrected as shown below:

Claim 2, column 4, line 31 after the word "determining" delete ---in---.

Signed and Sealed this

Third Day of November 1981

[SEAL]

Attest:

Attesting Officer

GERALD J. MOSSINGHOFF

Commissioner of Patents and Trademarks